(12) United States Patent
Richards et al.

(10) Patent No.: US 6,447,442 B1
(45) Date of Patent: Sep. 10, 2002

(54) INFANT CARE APPARATUS CANOPY FORCE LIMITING DEVICE

(75) Inventors: Andrew H. Richards, Westminster; Steven M. Falk, Baltimore, both of MD (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 09/632,431

(22) Filed: Aug. 4, 2000

Related U.S. Application Data

(60) Provisional application No. 60/170,264, filed on Dec. 11, 1999.

(51) Int. Cl.[7] .............................. A61G 10/02; H02P 1/04
(52) U.S. Cl. .......................................... 600/22; 318/430
(58) Field of Search ........................... 600/22; 318/430; 49/28; 73/862.231

(56) References Cited

U.S. PATENT DOCUMENTS

| | | | | |
|---|---|---|---|---|
| 5,101,595 A | * | 4/1992 | Rhoades ........................ | 49/28 |
| 5,453,077 A | * | 9/1995 | Donnelly et al. .............. | 600/22 |
| 5,641,916 A | * | 6/1997 | Satoh et al. ........... | 73/862.331 |
| 6,016,042 A | * | 1/2000 | Miura et al. ................. | 318/430 |
| 6,022,310 A | * | 2/2000 | Goldberg et al. ............. | 600/22 |
| 6,071,228 A | * | 6/2000 | Speraw et al. ................ | 600/22 |
| 6,224,539 B1 | * | 5/2001 | Jones et al. ................... | 600/22 |
| 6,231,499 B1 | * | 5/2001 | Jones .......................... | 600/22 |

\* cited by examiner

*Primary Examiner*—Eric F. Winakur
*Assistant Examiner*—Nikita R Veniaminov
(74) *Attorney, Agent, or Firm*—Roger M. Rathbun

(57) ABSTRACT

A safety system that is used with an infant care apparatus comprising an infant platform with a planar surface for supporting the infant and a canopy that is vertically movable over the planar surface. A powered lifting mechanism operated by an electric motor causes the canopy to be selectively moved upwardly or downwardly by the user to enclose or open the space surrounding the infant. The safety system provides a continuous monitor of the torque of the motor and, when the torque exceeds a predetermined amount, the system disables the motor so that it terminates any further movement of the canopy. Thus, if the canopy encounters an obstacle in its travel upwardly or downwardly, the motor torque will increase as the motor tries to overcome that obstacle and the system will immediately disable the motor and terminate any further movement of the canopy to prevent damage to the obstacle or to the powered lifting mechanism.

14 Claims, 3 Drawing Sheets

INFANT CARE APPARATUS CANOPY FORCE LIMITING DEVICE

Related Cases

The present application is based upon Provisional Patent Application Ser. No. 60/170,264, filed Dec. 11, 1999.

BACKGROUND

The present invention relates to an infant warming apparatus and, more particularly, to an apparatus for providing the combined functions of an infant incubator and an infant warmer with a movable canopy that travels vertically as the apparatus alternates between each function and where the canopy has a protective safety system.

There are, of course, many devices or apparatus for the warming of an infant and which supply the necessary heat to maintain the infant at a predetermined temperature. Of the various apparatus, there are infant warmers that are basically planar surfaces on which the infant is positioned and which planar surfaces generally include side guards to keep the infant safely within the confines of the apparatus. Infant warmers normally have an overhead radiant heater that is located above the infant and which thus radiates energy in the infrared spectrum to impinge upon the infant to maintain the infant at a warm, predetermined temperature. Since the infant is otherwise totally exposed to the surroundings, there is almost unlimited access to the infant by the attending personnel to perform various procedures on that infant. At typical infant warmer is shown and described in U.S. Pat. No. 5,474,517 of Falk et al and in the various prior are cited against that patent.

There are also infant incubators and which are more confined enclosures that contain the infant within an enclosed, controlled atmosphere that provides heat to the infant and also may provide control of humidity in the enclosed environment. Such incubators maintain the infant for long periods of time and there are handholes to access the infant and/or a larger door is provided that can be opened to access the infant or to insert or remove the infant to and from the incubator. Such devices provide a good atmosphere to the infant and control that local environment within which the infant is located, however, it is sometime difficult to perform a wide variety of procedures on the infant due to the somewhat limited access to that infant. A typical infant incubator is shown and described in U.S. Pat. No. 4,936,824 of Koch et al.

At the present, there are also certain infant care apparatus that combine the functions of an infant warmer and an incubator. One such apparatus is shown and described in U.S. Pat. No. 5,453,077 of Donnelly et al and which has an overhead canopy including an infrared heater and the canopy and heater are raisable and lowerable with respect to an infant positioned in the apparatus. Therefore, the device can operate as an incubator when the canopy and heater are in the lowered position and can act as an infant warmer when the canopy and the heater are in the upper position.

One difficulty, however, is in the use of a powered lifting mechanism to lift and lower the heater along with the canopy. With a normal lifting mechanism, the canopy and heater is raised and lowered by a motor or other powering device, however, there are times that the travel of the canopy should be stopped in it's movement due to some circumstance to avoid damage to the unit. As an example, if the canopy is being lowered by the user by means of the powered lifting mechanism, there is always the possibility that there may be some obstacle in the path of the travel of the canopy such as another device that may be in use affording care to the infant. In such case, if the canopy continues its powered downward travel, the canopy can strike the obstacle and either damage the canopy or its lifting mechanism or can damage the obstacle that may be an instrument or other device that can be relatively delicate.

According, it is important that some protection be afforded to the lifting mechanism for the canopy in the event such an obstacle is encountered either during the upward travel of the canopy or during its downward travel. Also, there is always the possibility that some part of the lifting mechanism, on its own, can fail and the lifting mechanism jam such that the further application of power trying to move the canopy can cause damage to the components of the lifting mechanism. In such case, it is important to have some safety system that disconnects the power to the lifting mechanism so that the damage is minimized or prevented altogether.

As a still further hazard, there may be times that the personnel put a heavy object atop of the canopy as a temporary measure and then an attempt is made to raise the canopy. In such case, the lifting mechanism can become overtaxed and be damaged be trying to raise a weight beyond its design capability. Again, it would be desirable to have a safety system that would recognize the potential hazard and take action to terminate the use of the lifting mechanism means immediately to prevent the likelihood of damage occurring.

SUMMARY OF THE INVENTION

Accordingly, the present invention relates to an infant care apparatus that has a movable canopy atop the apparatus that can be raised and lowered by a lifting mechanism. In the preferred embodiment, the invention relates to an infant care apparatus that combines the functions of an infant care warmer and an incubator and has a powered lifting mechanism to move a canopy upwardly and downwardly to change the functions of the apparatus.

In the present invention, there is provided an infant apparatus comprising an infant platform having a planar surface on which the infant rests and includes sides that extend upwardly from that surface. A canopy is mounted for vertical movement above the infant surface and has an upper position where it is above the surface and the sides and a lower position where the canopy mates with the upper peripheral combined edges of the upwardly extending sides to form an infant compartment to enclose the infant.

As such, the movement of the canopy between its upper and its lower positions is by means of a powered lifting mechanism that is powered by an electric motor. Accordingly, the user can activate the motor to move the canopy between its extreme positions. In the preferred embodiment, the canopy also carries a radiant heater to provide heat to the infant when the canopy is in its upper position.

A safety system is provided that can deactivate the motor, and along with it, the lifting mechanism during certain conditions that would otherwise cause damage to the equipment, other objects or personnel using the apparatus. In particular, the torque of the motor is continually sensed and monitored to determine the level of the motor torque. If that motor torque exceeds a predetermined value, the safety system disconnects the power to the motor or otherwise immediately terminates any further movement of the canopy, whether the canopy is moving upwardly or downwardly. Thus, the user can assess the situation and determine the cause of the problem in safety and without the danger of aggravating the possible harm to the lifting mechanism, object, or person encountered.

Therefore, in the case where canopy is moving downwardly by the user and the canopy encounters an obstacle in its travel, the increased torque of the motor is sensed and the motor immediately rendered inoperable by disconnecting the power to the motor. Thus, when the present safety system determines that an obstacle has been encountered by the canopy, such as where some other equipment has been left beneath the canopy, or even when a person obstructs the downward travel, the present system immediately terminates the further downward travel of the canopy by disabling the motor. In any event, the safety system prevents further damage to the obstacle, including a person, as well as to the lifting mechanism itself.

As can be seen, the system is operable as a safety system with the canopy moving in the upwardly or downwardly directions as the increase in the motor torque will still be sensed in the event any obstacle is encountered by the moving canopy and, as the increased torque exceeds the predetermined value, will disable the motor and with it, the further movement of the canopy in either direction.

Further, by the sensing of the motor torque, the motor will be disabled in the event it tries to lift a weight in excess of its designed capability. Thus, in the event a user leaves a heavy object atop of the canopy and tries to move the canopy upwardly with the heavy object still on the canopy the motor torque will again increase to the point where the motor will be disabled along with, of course, the lifting mechanism.

As another parameter in assessing the potential of damage, the change in torque may also be used as a gauge or limiting parameter, that is, the system may measure the torque of the motor and see if that torque changes significantly over a short period of time such as where the torque increases rapidly or at a high rate of increase. In such case, the system can take the preventative action to protect the infant care apparatus components and systems to avoid potential damage to those aforedescribed components and systems.

These and other features and advantages of the present invention will become more readily apparent during the following detailed description taken in conjunction with the drawings herein.

DETAILED DESCRIPTION OF THE INVENTION

Figure 1:
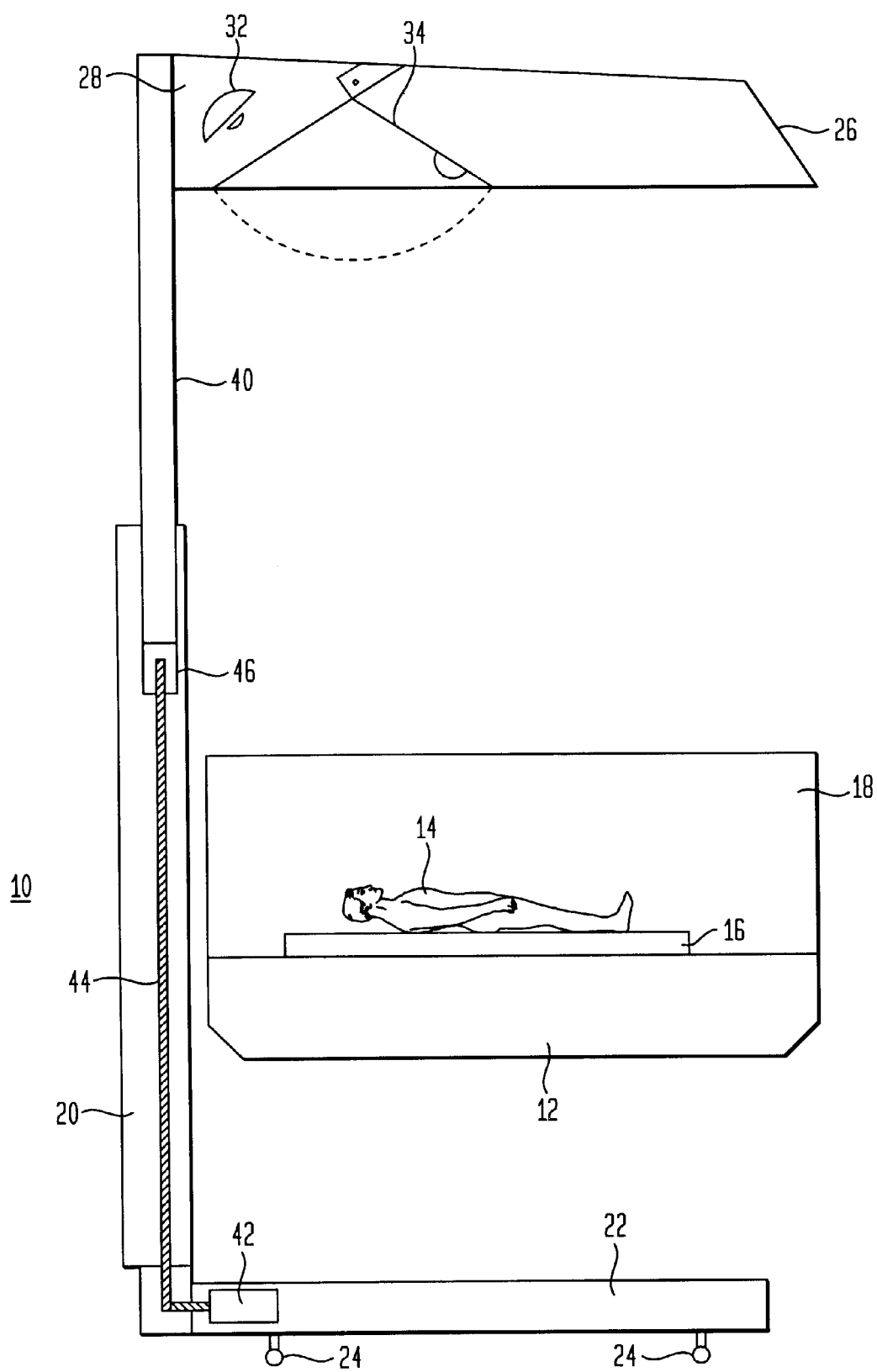
FIG. 1 is a schematic view of the infant warming apparatus constructed in accordance with the present invention wherein the radiant heater is shown in its upper position.

Referring now to FIG. 1, there is shown a schematic view of an infant warming apparatus 10 constructed in accordance with the present invention. As will be seen, the embodiment described here is the preferred embodiment where the apparatus can operate both as a normal incubator or, alternatively, as a radiant warmer, however, the invention is equally applicable where the apparatus is only an incubator or another infant care apparatus.

As shown, therefore, the infant warming apparatus 10 includes an infant platform 12 that supports and carries an infant 14 on a planar surface for ready access to treatment by attending personnel. An infant mattress 16 is also provided for the comfort of the infant. As is also seen, a plurality of walls 18 are provided to contain the infant safely within the infant warming apparatus 10 and may be positioned at all of the four sides of the infant platform 12. The walls 18 are preferably constructed of transparent plastic material and, as will be explained, cooperate with other components in order to provide an incubator function to the infant warming apparatus 10.

A vertical member 20 generally supports the infant platform 12 in cantilever fashion and the vertical member 20 may also have a supporting base 22 including wheels 24 to firmly support the infant platform 12 as well as the other components of the infant warming apparatus 10.

As also can be seen in FIG. 1, there is a canopy 26 that is positioned above the infant platform 12 and which contains a heater housing 28 in turn, containing a heater 32. As shown, in the preferred embodiment, the heater 32 is a radiant heater and, in the position of the canopy 26 as shown in FIG. 1, the heater 32 directs infrared energy downwardly to impinge upon the infant 14 to maintain that infant at a elevated temperature. It can be seen, however, that various other types of heaters can be used, including the infrared emitter shown and described in U.S. Pat. No. 5,474,517 of Falk et al.

In any event, the heater housing 28 also may include a movable door 34 that can be moved between an open position where the heater 32 is open to the surrounding environment and a closed position where the heater 32 is isolated and thus protected from the surrounding environment and is contained within the heater housing 28.

As indicated, the canopy 26 along with the heater 32 moves vertically with respect to the infant platform 12 and in FIG. 1, it is shown in its upper position. Although the actual raising and lowering of the canopy 26 may be by a variety of means, in FIG. 1, the embodiment comprises a vertical moving member 40 that supports canopy 26 in cantilever fashion. The vertical moving member 40 is raised and lowered by means of an electric motor 42 that is operated by a control system, controlled by the user or by an automatic system. The electric motor 42 rotates, in a controlled manner, a threaded screw 44 by a gear train that, in turn, is threadedly engaged to a threaded lug 46 fixed to the vertical moving member 40. Accordingly, as the electric motor 42 rotates in either direction, the vertical moving member 40 is caused to raise and lower to change the vertical position of the canopy 26 and, of course, the heater 32 correspondingly is raised and lowered.

As can be seen, the use of a gear train and threaded screw to move the canopy 26 between it upper and its lower position is preferred, however, as a alternative, a belt driven arrangement could also be used as well as other mechanisms providing, in accordance with the present invention, the system is operable or powered by an electric motor.

Figure 2:
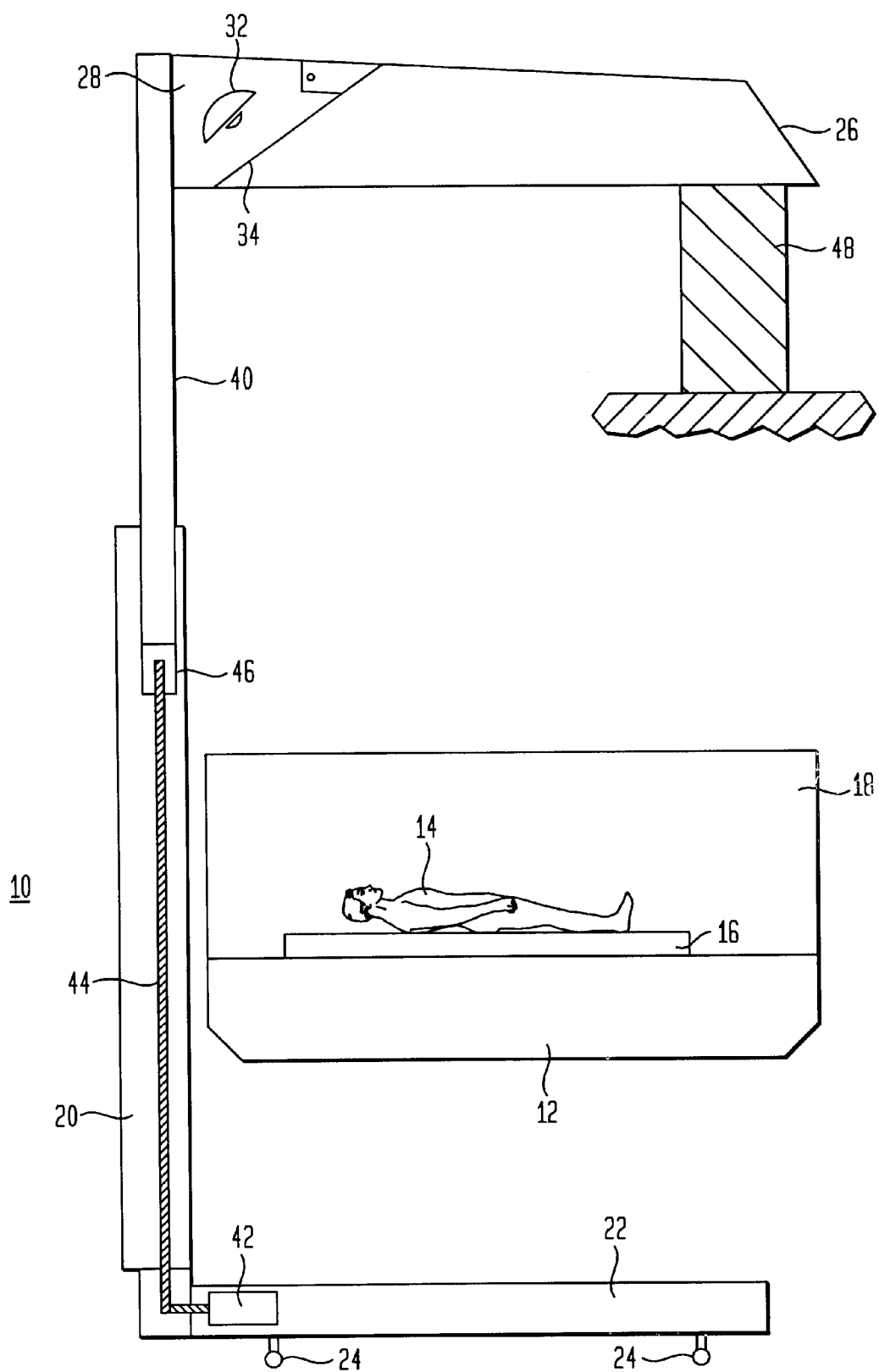
FIG. 2 is a schematic view of the apparatus of FIG. 1 but showing the radiant heater in an intermediate position encountering an obstacle.

Turning now to FIG. 2, there is shown a schematic view of the infant warming apparatus 10 of the present invention and where the canopy 26 and the heater 32 has moved to the intermediate position where the canopy 26 encounters an obstacle 48 and thus is unable to progress further downwardly. If, obviously, the obstacle 48 is relative immovable, the canopy 26 will continue to try to move downwardly and will cause real damage to the powered lifting mechanism such as strip the threads of the threaded screw 44, overheat the electric motor, or do other real damage to the system. Alternatively, the continued attempt to move downwardly can damage the obstacle 48. That obstacle may be a delicate instrument being used to monitor or otherwise care for the infant.

Accordingly, there is a safety system to prevent the foregoing from occurring and to prevent damage to the powered lifting system or other objects whenever the canopy 26 encounters an obstacle, either when traveling in the upward direction or in the downward direction.

Figure 3:
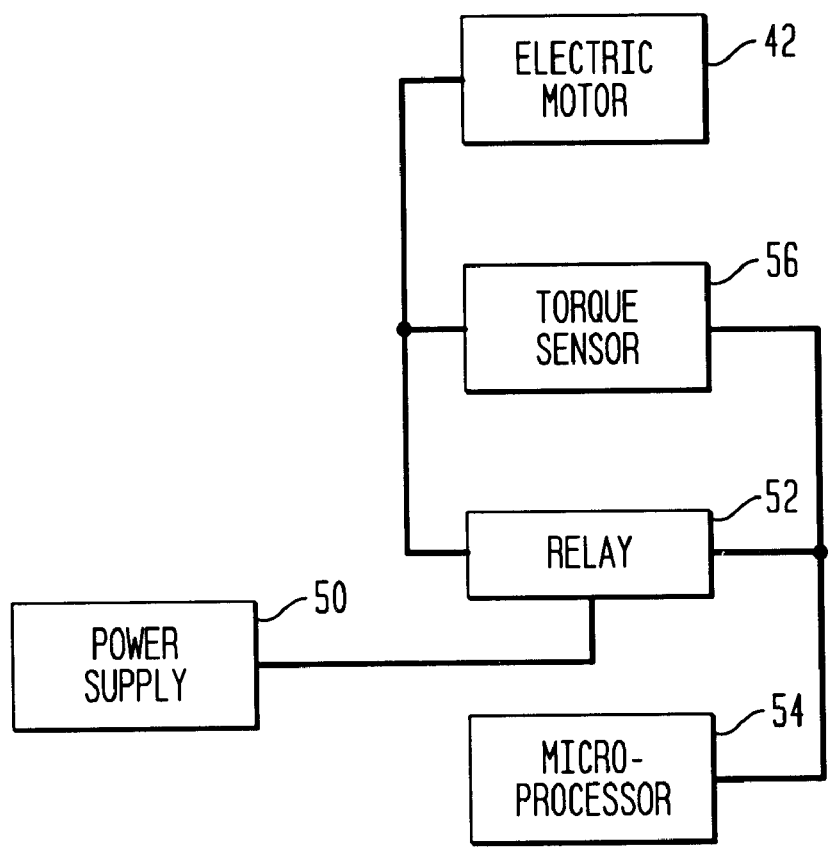
FIG. 3 is a block diagram of a typical control system usable with the present invention.

Turning finally to FIG. 3, taken along with FIGS. 1 and 2, there is shown a block diagram of a typical control system for providing safety system of the present invention. As can be seen, the electric motor 42 is operated from a source of electrical energy shown as power supply 50 through a relay 52. The active control of the motor 42 in its normal operation is by a microprocessor 54 and may operate by some action initiated by the user. In FIG. 3, there is also a torque sensor 56 that monitors the torque of the electric motor 42 to enable the safety system to know when the canopy has encountered an obstacle and the torque output of the motor has increased to attempt to overcome that obstacle. The torque sensor 56 thus continually monitors that torque and transmits the magnitude of the measured torque to the microprocessor 54 where there is stored in memory a predetermined torque output that would be considerably above the torque normally expended by the electric motor 42 in moving the canopy 26.

Thus, the microprocessor 54 determines when the torque measured by the torque sensor 56 exceeds that predetermined value and, when so sensed, sends a signal to the relay 52 to open the circuit to the electric motor 42 to disconnect the electric motor 42 thereby disabling the electric motor 42 and preventing the canopy 26 from moving any further.

Any further movement that could cause damage to the obstacle 48 or the powered lifting mechanism is thus prevented by the immediate disabling of the motor 42 when the predetermined torque has been determined. In the preferred embodiment, the torque sensor 56 is a current sensor that monitors the amperage to the motor and which is indicative of the torque output of the electric motor 42.

As an alternate parameter to monitor, the microprocessor 54 may monitor the level of the torque and also initiate some protective action in the even the torque changes rapidly over time, that is, if the level of the torque rises rapidly at a rate such that the microprocessor 54 determines that the rate of change of the torque exceeds a predetermined value limit in order to determine a fault condition and to take the appropriate action to prevent damage to the various components of the infant care apparatus. Thus, the system can not only use an increase in the level of torque as indicating a problem condition but also the change of torque over a predetermined period of time i.e. rate of change of the torque.

As may now be seen with respect to the safety system, by monitoring and disabling the electric motor 42 upon the motor torque exceeding a predetermined amount, the system will prevent damage in the event the canopy 26 encounters an obstacle either in the upward direction of travel or the downward direction and also protect the motor in the event user places a heavy load atop the canopy 26 and then attempt to raise the canopy 26. If the load atop the canopy 26, along with the normal load of the canopy 26 greatly exceeds the normal designed weight to be lifted by the electric motor 42, again the motor torque would become elevated to the point where that torque would exceed the predetermined amount, the power source to the motor would be disconnected and the electric motor 42 disabled immediately so that the motor and powered lifting mechanism cannot be damaged by the attempt to lift a load in excess of its design capability.

Those skilled in the art will readily recognize numerous adaptations and modifications which can be made to the infant care apparatus of the present invention which will result in an improved control system, yet all of which will fall within the scope and spirit of the present invention as defined in the following claims. Accordingly, the invention is to be limited only by the following claims and their equivalents.

We claim:

1. An infant care apparatus, said apparatus comprising a base having a surface on which an infant is positioned, a vertical member having mounted thereon a canopy movable along said vertical member between a lower position near said surface and an upper position, a lifting mechanism to move said canopy between said upper and said lower positions, said lifting mechanism including an electric motor adapted to be connected to a source of electrical energy, and a means for sensing the torque of said electric motor, said torque sensing means adapted to disconnect said source of electrical enemy to said electric motor when the torque sensed by said torque sensing means exceeds a predetermined amount or changes at a rate in excess of a predetermined value.

2. An infant care apparatus as defined in claim 1 wherein said torque sensing means senses current to said motor.

3. An infant care apparatus as defined in claim 1 wherein said canopy includes a radiant heater.

4. An infant care apparatus as defined in claim 1 wherein said lifting mechanism comprises a vertical member and a threaded screw, rotated by said motor that threadedly engages the vertical member to raise and lower said canopy.

5. An infant care apparatus, said apparatus comprising a base, an infant platform supported on said base and having a planar surface adapted to support an infant, a canopy mounted above said platform, said canopy being movable between a lower position where said canopy is near said infant platform and an upper position, a lifting mechanism adapted to move said canopy between said upper position and said lower position and having an electric motor, a controller for controlling said lifting mechanism to control the movement of said canopy, a torque sensor for sensing the output torque of said electric motor and providing a signal to said controller indicative of the output torque, said controller adapted to terminate movement of said canopy when said signal from said torque sensor indicates that the output torque is in excess of a predetermined amount or changes at a rate exceeding a predetermined value.

6. An infant care apparatus as defined in claim 5 wherein said controller is a central processing unit having a memory and wherein said predetermined torque output is retained in said memory.

7. An infant care apparatus as defined in claim 5 wherein said canopy includes a radiant heater.

8. An infant care apparatus as defined in claim 5 wherein said controller terminates movement of said canopy by shutting off electric power to said electric motor.

9. An infant care apparatus as defined in claim 5 wherein said torque sensor senses the electric current to said electric motor.

10. A method of providing safety in an infant apparatus, said method comprising:
   a. providing an infant platform for supporting an infant;
   b. providing a canopy above the infant platform that can be raised and lowered between an upper and a lower position, c. providing a lifting mechanism having an electric motor for raising and lowering the canopy,
d. monitoring the torque output of the electric motor and sensing when the torque output or the rate of change of the torque exceeds a predetermined amount,
e. controlling the lifting mechanism to prevent movement of the canopy when the torque output or rate of change of the torque in step (d) has exceeded that predetermined amount.

11. A method of providing safety in an infant apparatus as defined in claim 10 wherein said step of monitoring the torque output of the electric motor comprises monitoring the current to the motor.

12. A method of providing safety in an infant apparatus as defined in claim 10 wherein said step of controlling the lifting mechanism to prevent further movement of the canopy comprises shutting off the supply of electrical energy to the electric motor.

13. A method of providing safety in an infant apparatus as defined in claim 10 wherein said step of providing a canopy comprises providing a canopy having a radiant heater.

14. A method of providing safety in an infant apparatus as defined in claim 10 wherein said step of controlling the lifting mechanism comprises comparing the sensed torque output monitored with a predetermined torque amount.

* * * * *